US011369424B2

(12) United States Patent
Cho

(10) Patent No.: US 11,369,424 B2
(45) Date of Patent: Jun. 28, 2022

(54) ULTRASOUND APPARATUS OF BODY CAVITY INSERTABLE TYPE HAVING SEPARABLE SEALING COVER

(71) Applicant: KORUST CO., LTD., Anyang-Si (KR)

(72) Inventor: Sung-Chan Cho, Gunpo-Si (KR)

(73) Assignee: KORUST CO., LTD., Anyang-si (KR)

( * ) Notice: Subject to any disclaimer, the term of this patent is extended or adjusted under 35 U.S.C. 154(b) by 553 days.

(21) Appl. No.: 16/318,741

(22) PCT Filed: Oct. 12, 2018

(86) PCT No.: PCT/KR2018/012043
§ 371 (c)(1),
(2) Date: Jan. 18, 2019

(87) PCT Pub. No.: WO2020/075892
PCT Pub. Date: Apr. 16, 2020

(65) Prior Publication Data
US 2021/0000523 A1 Jan. 7, 2021

(30) Foreign Application Priority Data
Oct. 10, 2018 (KR) .................. 10-2018-0120299

(51) Int. Cl.
*A61B 18/04* (2006.01)
*A61B 18/00* (2006.01)

(52) U.S. Cl.
CPC ...... *A61B 18/04* (2013.01); *A61B 2018/0091* (2013.01); *A61B 2018/00327* (2013.01);
(Continued)

(58) Field of Classification Search
CPC .......... A61B 18/04; A61B 2018/00327; A61B 2018/0091; A61B 2018/00738;
(Continued)

(56) References Cited

U.S. PATENT DOCUMENTS 4,582,067 A * 4/1986 Silverstein ............. A61B 1/015
600/455
4,646,722 A * 3/1987 Silverstein ......... A61B 1/00073
600/104

(Continued)

FOREIGN PATENT DOCUMENTS

FR  2673542 A1  9/1992
JP  H10127678 A  5/1998
(Continued)

*Primary Examiner* — Oommen Jacob
(74) *Attorney, Agent, or Firm* — Rabin & Berdo, P.C.

(57) ABSTRACT

An ultrasound apparatus of a body cavity insertable type includes: a handpiece; a supporting rod which is elongated from the handpiece; an ultrasound probe which is connected to the supporting rod and is configured to be able to be inserted in the body cavity; and a sealing cover which is separably coupled to the ultrasound probe to at least partially surround the ultrasound probe in a longitudinal direction from a distal end thereof. The ultrasound probe includes: a piezoelectric element; and a housing to which the piezoelectric element is mounted. An end of the housing is connected to the supporting, and the housing is provided with an ultrasound passing hole which is disposed outside the supporting rod. The sealing cover has an ultrasound passing window which is formed at a position corresponding to the ultrasound passing hole.

16 Claims, 11 Drawing Sheets

(52) U.S. Cl.
CPC ............... *A61B 2018/00559* (2013.01); *A61B 2018/00738* (2013.01)

(58) Field of Classification Search
CPC .......... A61B 2018/00559; A61B 50/00; A61N 7/022; A61N 2007/0043; A61N 2007/0065; A61N 2007/0052; A61N 2007/0082; A61N 2007/022
See application file for complete search history.

(56) References Cited

U.S. PATENT DOCUMENTS

| | | | | |
|---|---|---|---|---|
| 4,947,827 A * | 8/1990 | Opie | ................ | A61B 1/00073 600/108 |
| 4,951,677 A * | 8/1990 | Crowley | ............. | A61B 5/6848 600/109 |
| 5,046,364 A * | 9/1991 | Stasuk | ................ | G10K 11/352 73/623 |
| 5,685,839 A * | 11/1997 | Edwards | ............ | A61B 18/1482 604/22 |
| 5,817,015 A * | 10/1998 | Adair | ................ | A61B 1/00174 600/121 |
| 5,954,940 A * | 9/1999 | Zdunek | ................ | G01N 17/02 205/776.5 |
| 6,626,855 B1 * | 9/2003 | Weng | ...................... | A61B 8/12 600/439 |
| 6,652,547 B2 * | 11/2003 | Rabiner | ........... | A61B 17/22012 606/159 |
| 6,669,655 B1 * | 12/2003 | Acker | ................ | A61B 17/2202 601/2 |
| 7,572,251 B1 * | 8/2009 | Davison | .............. | A61B 18/148 604/500 |
| 2002/0099289 A1 * | 7/2002 | Crowley | .................. | A61B 8/12 600/439 |
| 2005/0096642 A1 * | 5/2005 | Appling | ................. | A61B 18/24 606/15 |
| 2005/0154308 A1 | 7/2005 | Quistgaard et al. | | |
| 2005/0261586 A1 * | 11/2005 | Makin | .................. | A61B 8/4272 600/459 |
| 2005/0277811 A1 * | 12/2005 | Richards | ............ | A61B 1/00105 600/184 |
| 2006/0058680 A1 * | 3/2006 | Solomon | .............. | A61B 8/0833 600/466 |
| 2006/0259026 A1 * | 11/2006 | Godara | ............. | A61B 18/1482 606/41 |
| 2006/0264751 A1 * | 11/2006 | Wendelken | .......... | A61B 8/4281 600/439 |
| 2008/0027423 A1 | 1/2008 | Choi et al. | | |
| 2008/0064962 A1 * | 3/2008 | Oonuki | .................. | A61B 90/11 600/461 |
| 2009/0205665 A1 * | 8/2009 | Tanaka | .............. | A61M 39/0247 128/205.27 |
| 2012/0035473 A1 * | 2/2012 | Sanghvi | ............. | A61B 17/2251 600/439 |
| 2012/0265069 A1 * | 10/2012 | Sliwa | ....................... | A61B 8/12 600/439 |
| 2014/0243677 A1 * | 8/2014 | Johnson | .............. | A61B 8/4444 600/459 |
| 2014/0277034 A1 * | 9/2014 | Darian | ........... | A61B 17/320068 606/169 |
| 2021/0000523 A1 * | 1/2021 | Cho | ....................... | A61N 7/022 |

FOREIGN PATENT DOCUMENTS

| | | |
|---|---|---|
| JP | 2000-116656 A | 4/2000 |
| KR | 10-1191347 B1 | 10/2012 |
| KR | 10-2014-0111768 A | 9/2014 |
| KR | 101534434 B1 | 7/2015 |
| KR | 10-1857026 B1 | 5/2018 |
| KR | 10-1886673 B1 | 8/2018 |
| KR | 10-1896565 B1 | 9/2018 |

\* cited by examiner ously irradiating ultrasound in
ULTRASOUND APPARATUS OF BODY CAVITY INSERTABLE TYPE HAVING SEPARABLE SEALING COVER The present invention relates to an ultrasound apparatus of a body cavity insertable type which can be inserted into a body cavity such as a nasal cavity, an oral cavity, a pharynx, a vagina or the like and can perform an ultrasound treatment.

TECHNICAL FIELD

An ultrasound is used for various treatments and surgical procedures, and as an example a treatment method of treating diseases by noninvasively irradiating ultrasound in the tissues of a body cavity such as a nasal cavity has been introduced. A conventional ultrasound apparatus of a nasal cavity insertable type has a rod type supporting member which can be inserted into the nasal cavity and an ultrasound probe which is mounted on an end portion thereof. The ultrasound probe irradiates ultrasound in a state of being inserted into the nasal cavity, so a heat lesion is formed in the tissues within a nose in a noninvasive method to cure a disease such as a rhinitis.

Such an ultrasound apparatus of a nasal cavity insertable type has not yet been widely used, and technical progresses in various aspects such as an efficiency of an ultrasound irradiation, a stable structure and the like are required. In particular, depending on a kind of an ultrasound treatment, an enlargement of an area of irradiation of ultrasound and an increase of focusing density of an ultrasound may be required.

In particular, an ultrasound apparatus of a nasal cavity insertable type should be formed to be slender and long in order to be inserted into the nasal cavity and at the same time has a sufficient size of a piezoelectric element to generate ultrasound with a sufficient intensity. In addition, since the ultrasound energy cannot be transmitted without an ultrasound transmission medium, a structure for containing an ultrasound transmission medium should be effectively designed in a limited available space.

PRIOR ART DOCUMENT

1. Korean Patent Registration No. 10-1857026
2. Korean Patent Registration No. 10-1896565
3. Korean Patent Registration No. 10-1886673
4. US Patent Publication No. US2008/0027423

DETAILED DESCRIPTION OF THE INVENTION

Technical Problem

The present invention has been made in an effort to provide an ultrasound apparatus of a body cavity insertable type in which a size of a piezoelectric element can be maximized to increase an ultrasound energy, side effects of repeated uses of an ultrasound transmission film can be resolved, and assembling and manufacturing processes can be simplified to reduce manufacturing cost. Furthermore, the present invention has also been made in an effort to provide an ultrasound apparatus of a body cavity insertable type having means for preventing cross infections between patients.

Technical Solution

An ultrasound apparatus of a body cavity insertable type according to an embodiment of the present invention includes: a handpiece; a supporting rod which is elongated from the handpiece; an ultrasound probe which is connected to the supporting rod and is configured to be able to be inserted in the body cavity; and a sealing cover which is separably coupled to the ultrasound probe to at least partially surround the ultrasound probe in a longitudinal direction from a distal end thereof. The ultrasound probe includes: a piezoelectric element; and a housing to which the piezoelectric element is mounted. An end of the housing is connected to the supporting, and the housing is provided with an ultrasound passing hole which is disposed outside the supporting rod. The sealing cover has an ultrasound passing window which is formed at a position corresponding to the ultrasound passing hole.

The housing may form an ultrasound transmission space which is filled with an ultrasound transmission medium, and the piezoelectric element may be disposed in the ultrasound transmission space. The sealing cover may be configured to seal the ultrasound transmission medium filled in the ultrasound transmission space.

The sealing cover may include: a cover member which is put on the housing and forms the ultrasound passing window; and an ultrasound transmission film which is formed of material which can transmit an ultrasound and is attached to or is put on the cover member so as to cover the ultrasound passing window.

An indication or a structure for determining an insertion position of the sealing cover may be provided to at least one of the housing and the supporting rod.

A protrusion may be provided to one of the sealing cover and the supporting rod and an indentation into which the protrusion can be inserted is provided the other one of the sealing cover and the supporting rod, in order to determine an insertion position of the sealing cover.

At least one of a mark indicating an insertion depth into the body cavity and a mark indicating an irradiation direction of an ultrasound may be indicated on the sealing cover.

The sealing cover may be provided with an ultrasound generation position mark which indicates a position of the piezoelectric element in a state of being put on the ultrasound probe.

A mark which indicates an irradiation direction of an ultrasound may be provided to the handpiece.

The sealing cover may be made of a flexible thin film.

The housing may be provided with a through hole which is disposed at the rear side of the piezoelectric element, and further comprising a rear cover which covers the through hole.

The ultrasound transmission medium may be liquid, and the ultrasound apparatus may further include an inlet hose and an outlet hose respectively for introducing the ultrasound transmission medium into the ultrasound transmission space and for discharging the ultrasound transmission medium from the ultrasound transmission space.

An entrance portion of the sealing cover may have a widened shape.

Advantageous Effects

According to the present invention, a size of a piezoelectric element can be maximized under given conditions so as to increase an ultrasound energy. Furthermore, by attaching an ultrasound transmission film to a separable sealing cover, the side effects caused by repeated uses of an ultrasound transmission film can be resolved and the assembling and manufacturing processes can be simplified. Furthermore, since a sealing cover can be replaced, a cross infection between patients can be prevented.

DETAILED DESCRIPTION OF THE EMBODIMENTS

Figure 1:
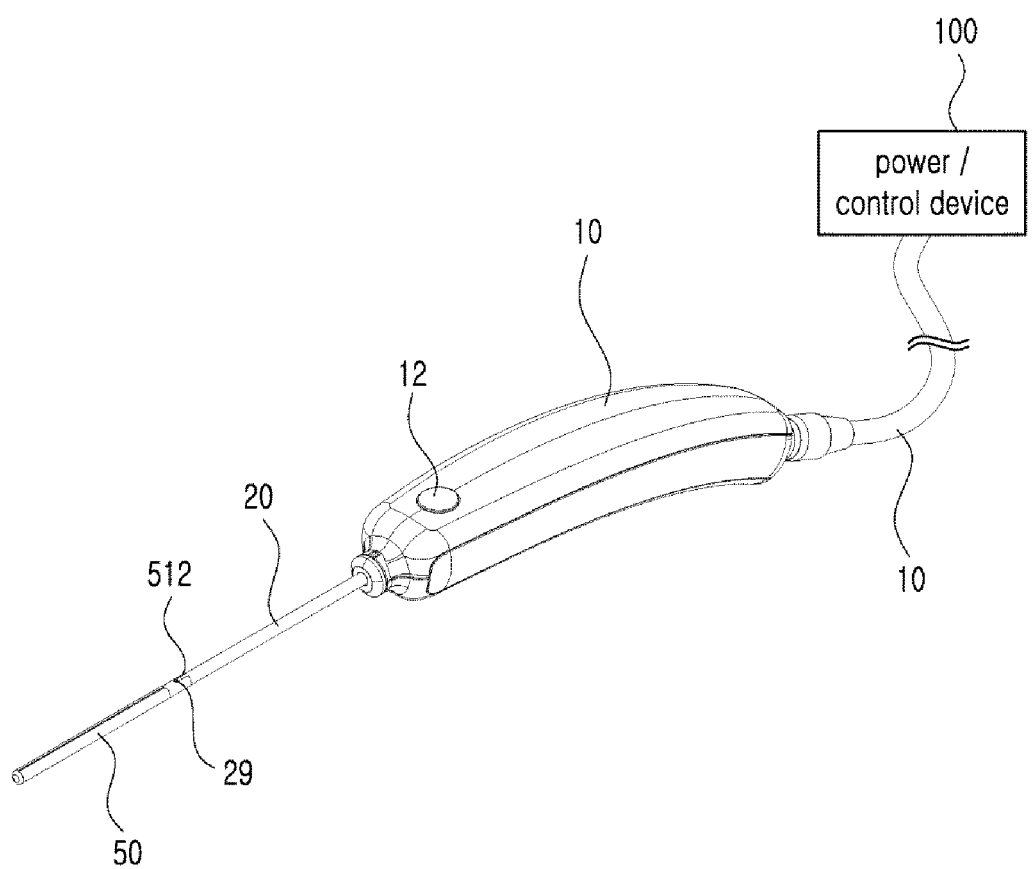
FIG. 1 is a perspective view of an ultrasound apparatus of a body cavity insertable type according to an embodiment of the present invention.

Embodiments of the present invention will be described in detail with reference to the accompanying drawings hereinafter.

An ultrasound apparatus of a body cavity insertable type according to an embodiment of the present invention is configured to be able to irradiate ultrasound in a state of being inserted into a body cavity such as a nasal cavity, an oral cavity, a pharynx, and a vagina to make heat lesion in the tissues. Referring to FIG. 1 to FIG. 4, an ultrasound apparatus according to an embodiment of the present invention includes a handpiece 10, a supporting rod 20, an ultrasound probe 30 and a separable sealing cover 50.

The handpiece 10 may be formed to be able to be grasped by a hand of an operator performing an ultrasound treatment. As exemplarily shown in FIG. 1, the handpiece 10 may be configured to be connected to an external power/control device 100 via an electric power cable 11, and may be provided with an on/off button 12 to regulate an ultrasound generation by an on/off of an electric power. The power/control device 100 may be configured to provide electric power for the generation of ultrasound and various controls for and ultrasound treatment. The handpiece 10 may be separately formed and may be connected to the electric power cable 11, or may be formed as a separate part including the electric power cable 11 and may be connected to the power/control device 100.

The supporting rod 20 may be extended from the handpiece 10 and may have a shape of a long rod. Since a distal end portion of the supporting rod 20 may be inserted into the nasal cavity or the like during an ultrasound treatment, the supporting rod 20 is formed as a rod shape having a relatively small diameter which can be inserted into the body cavity. As shown in FIG. 1, the supporting rod 20 is extended from a distal end of the handpiece 10. At this time, the supporting rod 20 may be formed a part separated from the handpiece 10 to be connected to the handpiece 10, or may be formed integrally with the handpiece 10.

Figure 2:
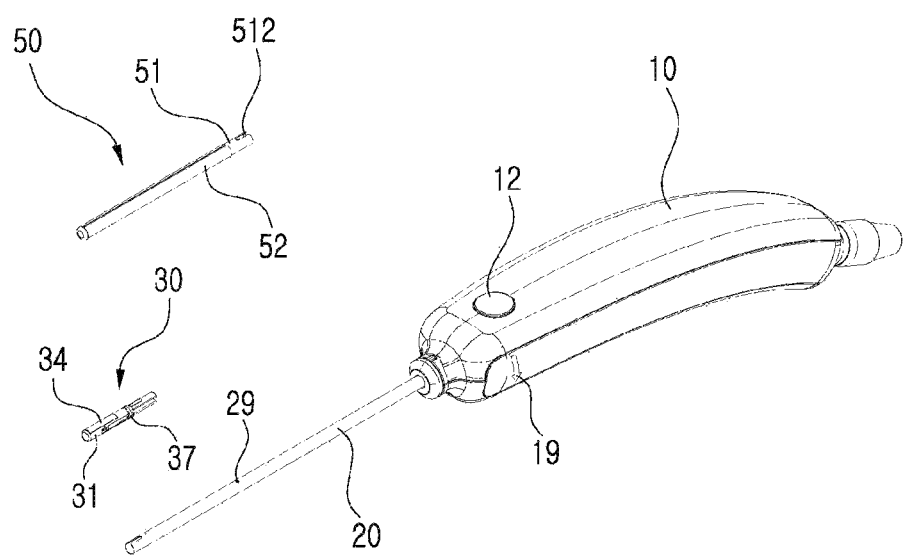
FIG. 2 is an exploded perspective view of an ultrasound apparatus of a body cavity insertable type according to an embodiment of the present invention.
Figure 4:
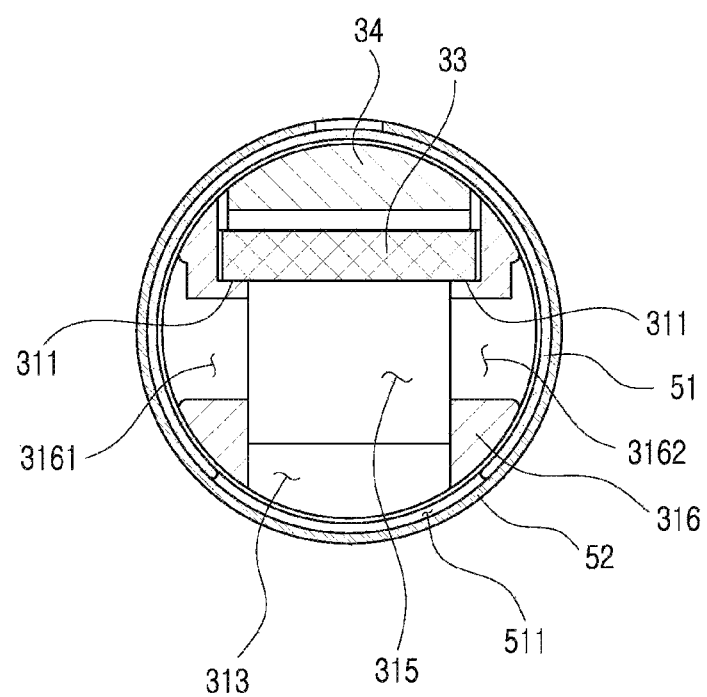
FIG. 4 is a laterally-taken sectional view of a supporting rod, an ultrasound probe and a sealing cover of an ultrasound apparatus of a body cavity insertable type according to an embodiment of the present invention.

The ultrasound probe 30 causes an ultrasound vibration due to the application of a pulsed electric power. Referring to FIG. 2 and FIG. 4, the ultrasound probe 30 includes a housing 31 and a piezoelectric element 33. The piezoelectric element 33 may be formed by forming a pair of electrodes on both sides of a piezoelectric material layer such as a piezoelectric ceramic layer as well known in the art, and is configured such that the piezoelectric material layer vibrates when a pulsed electric power is applied to both electrodes. Not shown in the drawings, electric cables may be provided to apply the pulsed electric power to the electrodes of the piezoelectric element 33. For example, the electric cables may be electrically connected to the electrodes of the both sides of the piezoelectric element 33 after passing through the handpiece 10, the supporting rod 20 and the housing 31.

Figure 3:
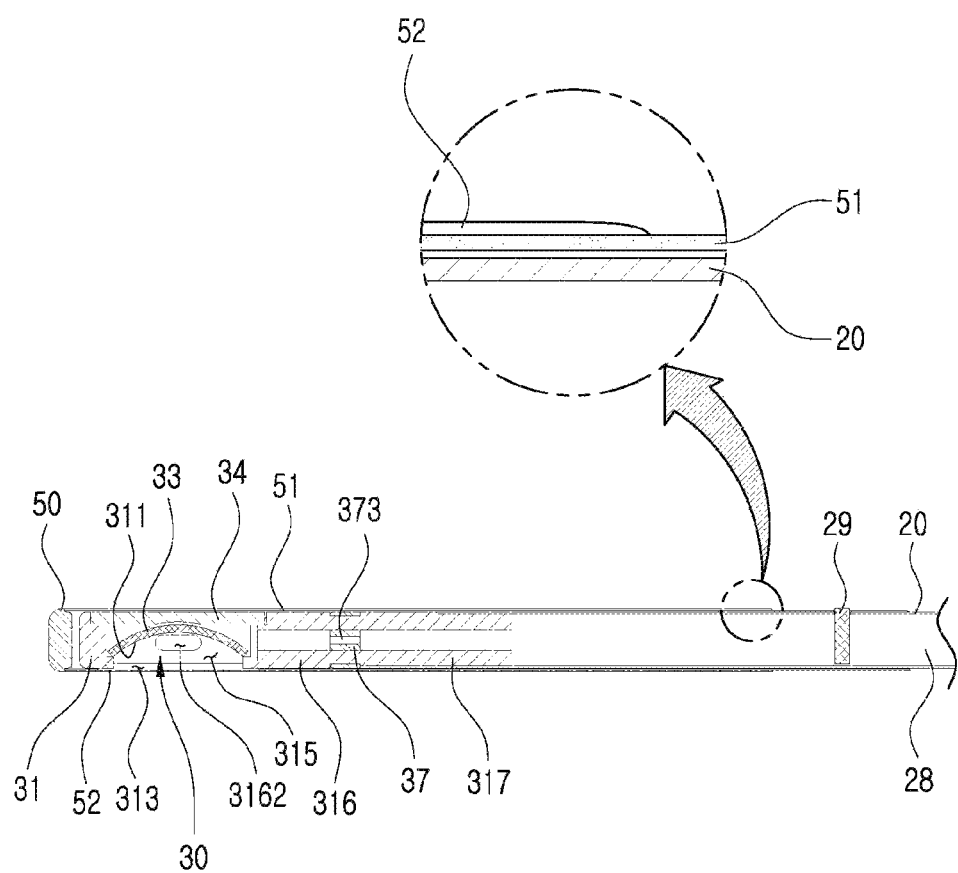
FIG. 3 is a longitudinally-taken sectional view of a supporting rod, an ultrasound probe and a sealing cover of an ultrasound apparatus of a body cavity insertable type according to an embodiment of the present invention.

The housing 31 of the ultrasound probe 30 is connected to the supporting rod 20 and is configured to be able to be inserted into the body cavity such as the nasal cavity. The housing 31 may include a piezoelectric element mounting portion 316 to which the piezoelectric element 33 is mounted and an insertion portion 317 for the connection with the supporting rod 20. At this time, the piezoelectric element mounting portion 316 may form a mounting space 315 into which the piezoelectric element 33 is disposed, and a frontal space of the piezoelectric element 33 may be filled with an ultrasound transmission medium. For example, as shown in FIG. 3, the supporting rod 20 may be formed to have a hollow tube having an insertion hole 28 which is elongated along a longitudinal direction. The insertion portion 317 of the housing 31 is formed to have a diameter slightly less than an inner diameter of the insertion hole 28 and may be fitted into the insertion hole 28 of the supporting rod 20. At this time, according to an embodiment of the present invention, a diameter of the piezoelectric element mounting portion 316 may be greater than the diameter of the insertion portion 317. Accordingly, the size of the piezoelectric element 33 can be increased by the increase of the piezoelectric element mounting portion 316, and thus the ultrasound energy can be increased.

The supporting rod 20 may be formed of metal in order to secure a required durability and a structural strength, and the housing 31 may be formed of electrical insulation material for electric insulation with the piezoelectric element 33.

The piezoelectric element mounting portion 316 of the housing 31 forms an ultrasound passing hole 313 through which ultrasound generated by the piezoelectric element 33 passes. For example, the piezoelectric element mounting portion 316 may be disposed to irradiate ultrasound in a downward direction in FIG. 4, and accordingly the ultrasound passing hole 313 may be formed at a lower portion of the housing 31. The ultrasound generated by the piezoelectric element 33 progresses into tissues of the body cavity after having passed the ultrasound passing hole 313.

The piezoelectric element 33 may be disposed to irradiate ultrasound in a direction (downward direction in FIG. 3) perpendicular to a longitudinal direction (horizontal direction in FIG. 3) of the housing 31. Accordingly, in a state of being inserted into the body cavity, the piezoelectric element 33 can easily irradiate ultrasound into tissues of the body cavity. The ultrasound passing hole 313 of the housing 31 is also formed at an area perpendicular to a longitudinal direction.

The housing 31 may form an ultrasound transmission space 315 which is connected to the ultrasound passing hole 313 and is filled with the ultrasound transmission medium. As shown in FIG. 2 and FIG. 3, one surface of the piezoelectric element 33 is exposed to the ultrasound transmission space 315, and the ultrasound transmission space 315 is filled with the ultrasound transmission medium of gel or liquid.

Referring to FIG. 3 and FIG. 4, the piezoelectric element 33 may have a curvature about a direction (depth direction in FIG. 3) perpendicular to a longitudinal direction (horizontal direction in FIG. 3) of the supporting rod 20. That is, as shown in FIG. 3, the curved surface of the piezoelectric element 33 is elongated in a longitudinal direction of the supporting rod 20, i.e., in an insertion direction into the body cavity. Due to this configuration of the curved surface, the structure of the ultrasound probe 30 of a long rod shape which can be inserted into the body cavity can be realized. The piezoelectric element 33 may have a concave surface, a shape obtained by removing both sides of a concave surface, a cylindrical surface, a bended cylindrical surface which is obtained by bending inwardly both side portions of a cylindrical surface.

A portion of the housing 31 facing the rear surface of the piezoelectric element 33 may be removed for the installation of the piezoelectric element 33, and a rear cover 34 which covers this removed portion after the installation of the piezoelectric element 33 may be provided. If the ultrasound transmission medium flows into the rear space of the piezoelectric element 33 through the rear side of the housing 31, the piezoelectric element 33 may be broken or damaged by electrical short. In order to prevent this, the rear side of the housing 31 may be sealed by putting on a separate cover in order to prevent the ultrasound transmission medium from flowing into the rear space of the piezoelectric element 33.

Figure 5:
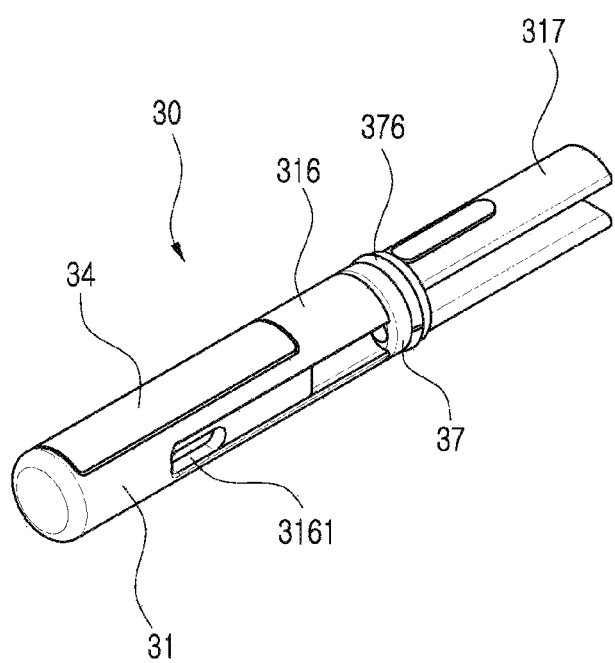
FIG. 5 is a perspective view of an ultrasound probe of an ultrasound apparatus of a body cavity insertable type according to an embodiment of the present invention.
Figure 6:
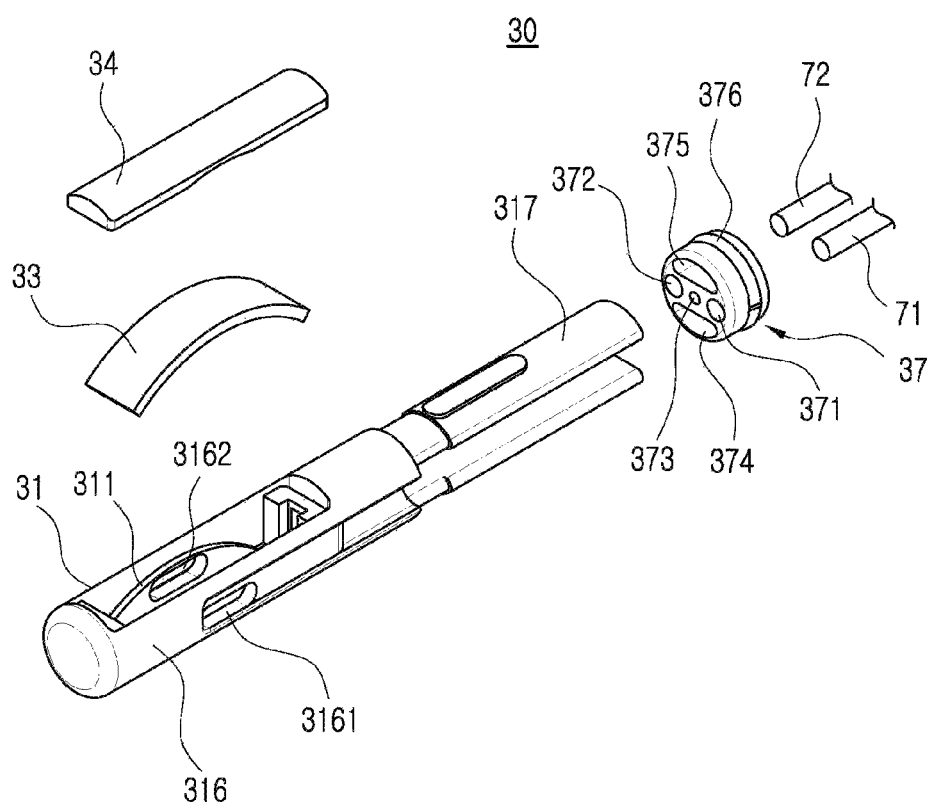
FIG. 6 is an exploded perspective view of an ultrasound probe of an ultrasound apparatus of a body cavity insertable type according to an embodiment of the present invention.
Figure 7:
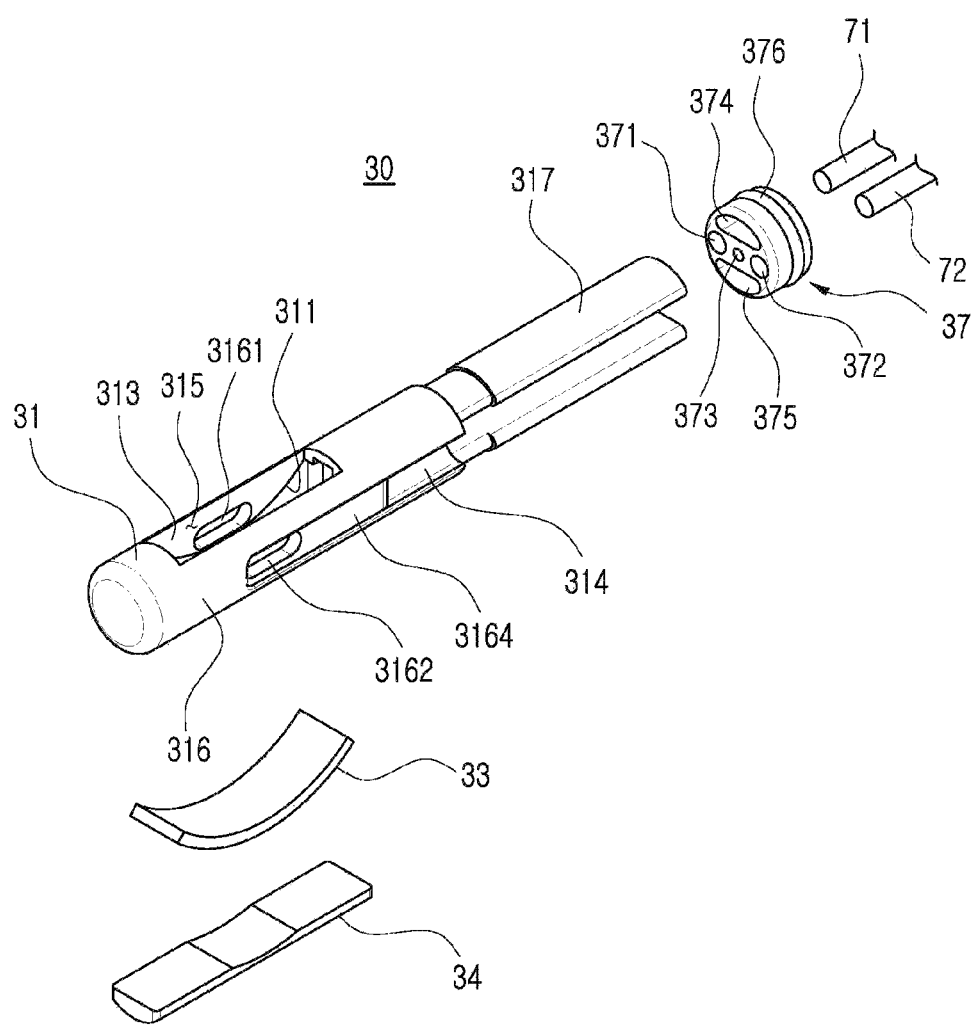
FIG. 7 is an exploded bottom perspective view of an ultrasound probe of an ultrasound apparatus of a body cavity insertable type according to an embodiment of the present invention.

Referring to FIG. 7, in case that the ultrasound transmission space 315 is filled with an ultrasound transmission medium of a liquid state, the housing 31 may be provided with passages 3162 and 3161 for inlet and outlet of the ultrasound transmission medium. The ultrasound transmission space 315 may be connected to a reservoir (not shown) containing the ultrasound transmission medium via an inlet hose 72 and an outlet hose 71. At this time, the inlet hose 72 and the outlet hose 71 may penetrate a sealing member 37. The sealing member 37 may be provided with through holes 372 and 371 through which the inlet hose 72 and the outlet hose 71 pass respectively, and the inlet hose 72 and the outlet hose 71 passing through the supporting rod 20 pass the through holes 372 and 371 of the sealing member 37 to be fluidically connected to the passages 3162 and 3161 of the housing 31. Referring to FIG. 5 to FIG. 7, the insertion portion 317 of the housing 31 may be formed two separate portions, and the sealing member 37 may have two through holes 374 and 375 into which the two portions of the insertion portion 317 are respectively inserted. The ultrasound transmission medium can be prevented from flowing into the supporting rod 20 by the sealing member 37. Not shown in the drawings, a pump for circulating ultrasound transmission medium may be provided.

Meanwhile, the housing 31 may have a passage through which electric cables for electrically connecting both electrodes of the piezoelectric element 33, and this passage may be connected to the rear side of the piezoelectric element 33 for a sealing of the ultrasound transmission medium. At this time, the sealing member 37 may be provided with a through hole 373 through which the electric cable passes, and the electric cable may be connected to the piezoelectric element 33 after having passed the supporting rod 20 and the through hole 373.

The sealing cover 50 is separably connected to the ultrasound probe 30 so as to at least partially enclose the ultrasound probe 30 from a distal end thereof. The ultrasound treatment may be performed in a state of coupling the sealing cover 50 to the ultrasound probe 30.

The sealing cover 50 may include a cover member 51 having a tube shape one end of which is closed. The cover member 51 may have an ultrasound passing window 511 which is formed at a position corresponding to the ultrasound passing hole 313 of the housing 31. In case that the ultrasound transmission space 315 is filled with an ultrasound transmission medium of a liquid state, an ultrasound transmission film 52 for sealing the ultrasound passing window 511 may be attached to the cover member 51 or may be put on the cover member 51. For example, the ultrasound transmission film 52 may be attached to an outer surface of the cover member 51 by a double-sided adhesive tape. Meanwhile, in another embodiment, the ultrasound transmission film 52 may be formed in a type of a condom which is made of thin film, and by putting the ultrasound transmission film 52 on the cover member 51, the ultrasound passing window 511 can be sealed.

A sealing mechanism for preventing the ultrasound transmission medium from leaking between the housing 31 and the sealing cover 50 even when the sealing cover 50 is coupled to the housing 31. According to an embodiment of the present invention, the sealing mechanism may include an annular sealing protrusion 376 which is formed on the sealing member 37. The annular sealing protrusion 376 may be formed by being radially outwardly protruded, and tightly contacts an inner circumferential surface of the cover member 51 of the sealing cover 50 in a state that the sealing cover 50 is coupled. Accordingly, the ultrasound transmission medium filled with the ultrasound transmission space 115 can be prevented from leaking to the outside. In order to enhance the sealing effect, the sealing member 37 may be made of rubber or silicon. Further, since the inlet hose 72 and the outlet hose 71 pass through the sealing member 37 and the sealing member 37 is fitted into the supporting rod 20, the ultrasound transmission medium filled in the housing 31 can be prevented from leaking into the supporting rod 20.

In another embodiment of the present invention, the sealing mechanism may be an O-ring which is connected to the housing 31. The annular sealing protrusion 376 can prevent the ultrasound transmission medium from leaking to the outside and at the same time can prevent the ultrasound transmission medium from flowing into the supporting rod 20. In particular, since it is difficult to make a separate sealing mechanism if the diameters of the insertion portion 317 of the housing 13 and the supporting rod 20 are very small, the annular sealing protrusion 376 provides not only a sealing between the sealing cover 50 and the housing 31 but also a sealing between the housing 31 and the supporting rod 20. In addition, the annular sealing protrusion 376 can play a role of preventing the separation of the sealing cover 50. For example, the annular sealing protrusion 376 can prevent the separation of the sealing cover 50 during the filling of the ultrasound transmission medium after coupling the sealing cover 50 to the housing 31 or during the ultrasound treatment. At this time, alternatively, in order to prevent the separation of the sealing cover 50, an end portion of the sealing cover 50 coupled to the housing 31 can be attached by an adhesive tape.

The sealing cover 50 may be formed of metal, synthetic resin or the like. The sealing cover 50 may be formed of transparent material in order to allow a user to see the filling state of the ultrasound transmission medium in the housing 31. Meanwhile, in another embodiment, the sealing cover is made of nontransparent material, and a transparent window may be provided to the sealing cover in order to check the filling state of the ultrasound transmission medium.

Meanwhile, not shown in the drawings, a fixing means for preventing the separation of the coupled sealing cover 50. For example, the separation of the sealing cover 50 can be prevented by a fixing means such as an adhesive tape, a coupling thread, a tight fitting or the like.

According to an embodiment of the present invention, an entrance of the cover member 51 of the sealing cover 50 can be outwardly widened in order to make the sealing cover 50 be easily put on.

According to an embodiment of the present invention, in order to make it easy to insert the sealing cover 50 at a predetermined position, an indication or a structure for indicating an insertion position of the sealing cover 50 can be provided at least one of the sealing cover 50 and the supporting rod 20. For example, referring to FIG. 1 and FIG. 2, in order to insert the housing 31 into the sealing cover 50 in a state that the ultrasound passing window 511 of the sealing cover 50 corresponds to the position of the ultrasound passing hole 313 of the hosing 31, an indentation 512 is formed to the cover member 51 of the sealing cover 50 and a protrusion 29 may be provided to the supporting rod 20. By coupling the sealing cover 50 such that the protrusion 29 of the supporting rod 20 is inserted into the indentation 512 of the cover member 51, the precise insertion position of the sealing cover 50 can be determined. Meanwhile, in another embodiment, the cover member 51 has a protrusion and the supporting rod 20 may have an indentation. Meanwhile, in yet another embodiment, rather than the indentation and the protrusion, other indication for an insertion position such as a mark, a symbol, or a figure can be used.

Figure 8:
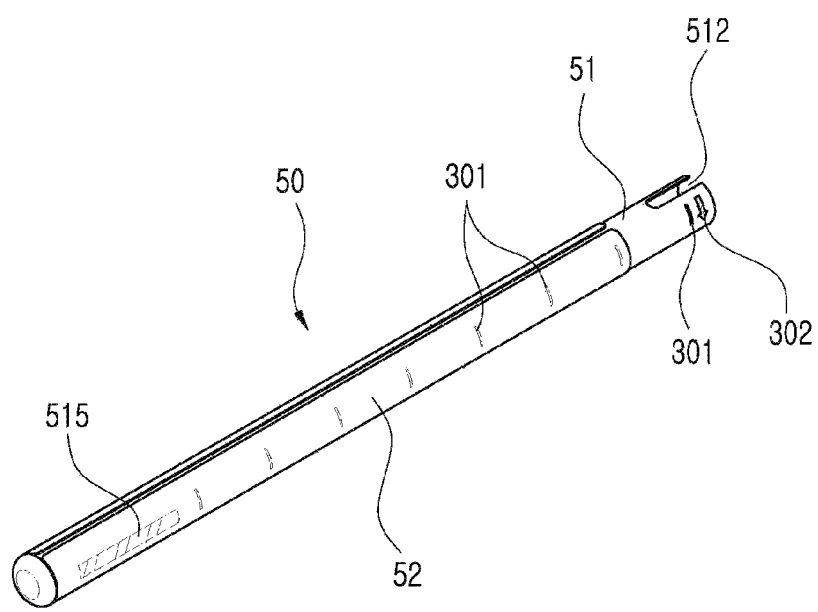
FIG. 8 is a perspective view of a sealing cover of an ultrasound apparatus of a body cavity insertable type according to an embodiment of the present invention.
Figure 9:
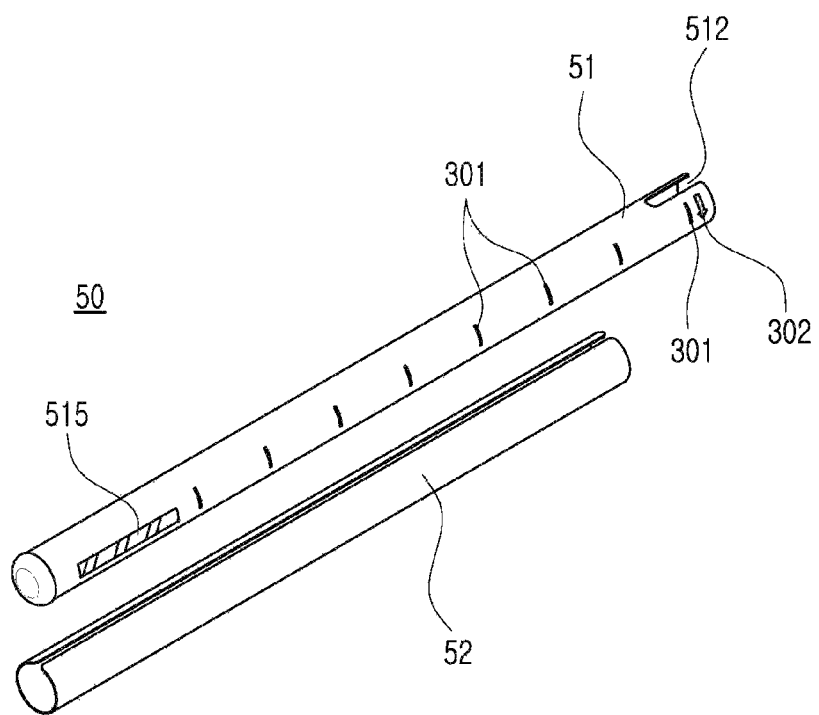
FIG. 9 is an exploded perspective view of a sealing cover of an ultrasound apparatus of a body cavity insertable type according to an embodiment of the present invention.

Referring to FIG. 8 and FIG. 9, at least one of a mark 301 indicating the ultrasound irradiation position and a mark 303 indicating an irradiation direction of ultrasound may be indicated on the sealing cover 50. An irradiation position of the ultrasound can be estimated on the basis of a relative position of the mark 301 from an inlet of a nose, and a direction of an irradiation of an ultrasound can be known from the mark 303. For example, the mark 301 indicating the ultrasound irradiation position may be indicated on the cover member 51 and the ultrasound transmission film 52 is formed of transparent material, so the mark 301 can be seen. In another embodiment, the mark indicating the ultrasound irradiation position and the mark indicating an irradiation direction of an ultrasound may be indicated on the ultrasound transmission film.

Figure 10:
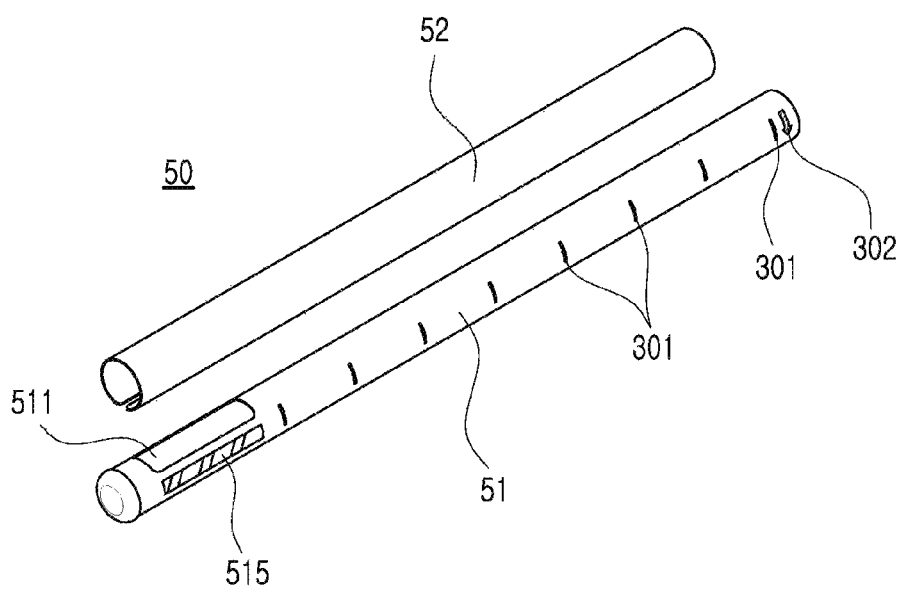
FIG. 10 is an exploded bottom perspective view of a sealing cover of an ultrasound apparatus of a body cavity insertable type according to an embodiment of the present invention.

According to another embodiment, as shown in FIG. 8 to FIG. 10, the sealing cover 50 may have an ultrasound generation position mark 515 which indicates a position of the ultrasound probe 30, i.e., the position of the piezoelectric element 33 connected to the housing 31. The ultrasound generation position mark 515 may be formed at a side of the cover member 51 or at a surface opposite the through hole, and as shown in FIG. 8 the ultrasound transmission film 52 may be made of transparent material such that the ultrasound generation position mark 515 can be seen from the outside. Alternatively, the ultrasound generation position mark 515 can be indicated on the ultrasound transmission film 52. An ultrasound treatment can be performed by inserting the ultrasound probe 30 coupled with the sealing cover 50 into the body cavity while seeing an image of the ultrasound probe 30 obtained by an endoscope, and at this time it is possible to irradiate the ultrasound at a desired position by seeing the ultrasound generation position mark 515.

Meanwhile, referring to FIG. 1, a mark 19 indicating a direction of an ultrasound irradiation can be formed on the handpiece 10.

Figure 11:
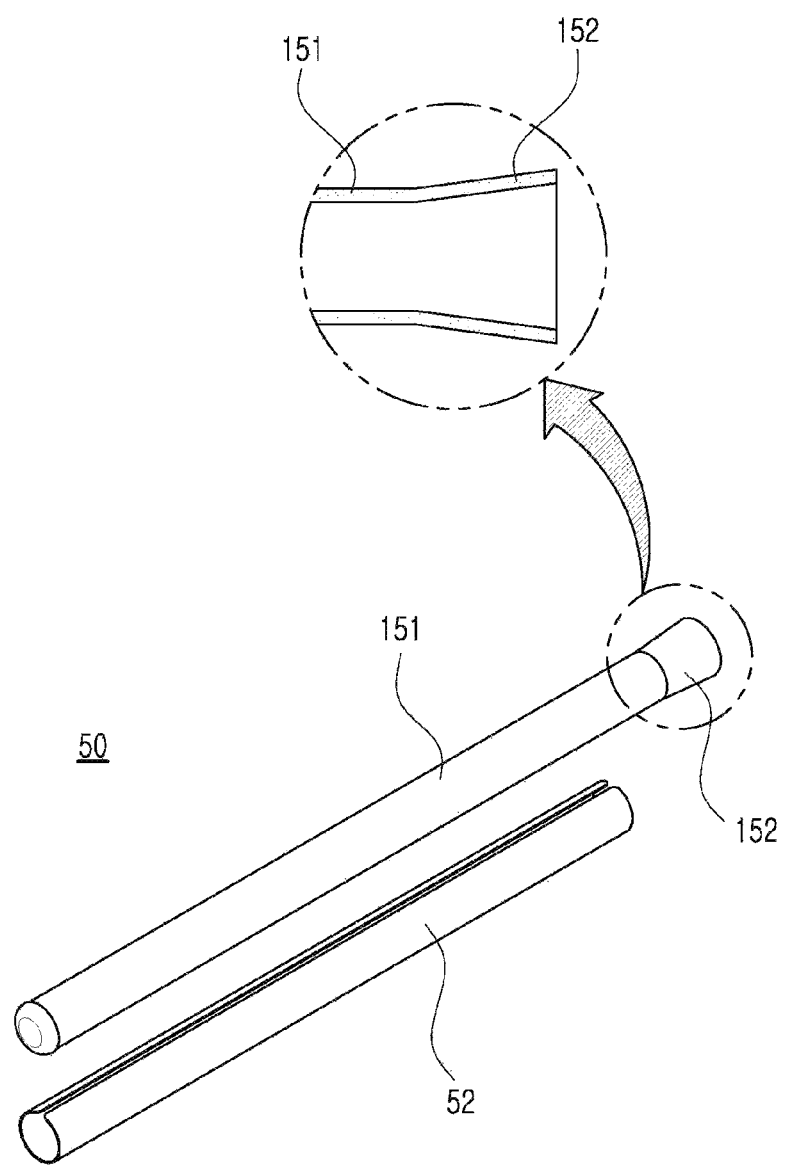
FIG. 11 is a longitudinally-taken sectional view of a sealing cover of an ultrasound apparatus of a body cavity insertable type according to an embodiment of the present invention.

Referring to FIG. 11, according to another embodiment of the present invention, an end portion of an entrance of the sealing cover 151 may have a widened shape. For example, as shown in FIG. 11, a slanted portion 152 having increasing inner diameter may be provided at an end portion of an entrance of the sealing cover 151. Accordingly, the sealing cover 150 can be easily put on the housing 31.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The present invention relates to an ultrasound apparatus of a body cavity insertable type which can be used for an ultrasound treatment to have an industrial applicability.

The invention claimed is:

1. An ultrasound apparatus of a body cavity insertable type, comprising:
a handpiece;
a supporting rod which is elongated from the handpiece;
an ultrasound probe which is connected to the supporting rod and is configured to be able to be inserted in a body cavity; and
a sealing cover which is separably coupled to the ultrasound probe to at least partially surround the ultrasound probe in a longitudinal direction from a distal end thereof,
wherein the ultrasound probe comprises:
a piezoelectric element; and
a housing to which the piezoelectric element is mounted and defining an ultrasound transmission space that is filled with an ultrasound transmission medium, an end of the housing being connected to the supporting rod, the housing being provided with an ultrasound passing hole which is disposed outside the supporting rod,
wherein the sealing cover comprises:
a sheath-shaped cover member that has an ultrasound passing window which is formed at a position corresponding to the ultrasound passing hole and is configured to be separably put on the housing; and
an ultrasound transmission film that is formed of material that can transmit an ultrasound and is configured to be attached to or to be on the sheath-shaped cover member so as to cover the ultrasound passing window; and wherein the sealing cover is configured to be at least partially transparent so that the ultrasound transmission medium filled in the ultrasound transmission space can be seen via the sealing cover.

2. The ultrasound apparatus of claim 1, further comprising a sealing mechanism which is interposed between an outer surface of the housing and the sealing cover.

3. The ultrasound apparatus of claim 2, wherein the sealing mechanism comprises a sealing member which is connected to the housing and is configured to prevent the ultrasound transmission medium from leaking from the ultrasound probe.

4. The ultrasound apparatus of claim 3, wherein the sealing member comprises a sealing protrusion which is outwardly protruded in a radial direction and contacts an inner circumferential surface of the cover member.

5. An ultrasound apparatus of a body cavity insertable type, comprising:
   a handpiece;
   a supporting rod which is elongated from the handpiece;
   an ultrasound probe which is connected to the supporting rod and is configured to be able to be inserted in a body cavity;
   a sealing cover which is separably coupled to the ultrasound probe to at least partially surround the ultrasound probe in a longitudinal direction from a distal end thereof; and
   a sealing mechanism which is interposed between an outer surface of the housing and the sealing cover;
   wherein the ultrasound probe comprises:
   a piezoelectric element; and
   a housing to which the piezoelectric element is mounted and defining an ultrasound transmission space that is filled with an ultrasound transmission medium, an end of the housing being connected to the supporting rod, the housing being provided with an ultrasound passing hole which is disposed outside the supporting rod;
   wherein the sealing cover comprises:
   a sheath-shaped cover member that has an ultrasound passing window which is formed at a position corresponding to the ultrasound passing hole and is configured to be separably put on the housing; and
   an ultrasound transmission film that is formed of material that can transmit an ultrasound and is configured to be attached to or to be on the sheath-shaped cover member so as to cover the ultrasound passing window; and
   wherein the sealing mechanism comprises a sealing member which is connected to the housing and is configured to prevent the ultrasound transmission medium from leaking from the ultrasound probe;
   the ultrasound apparatus further comprising an inlet hose and an outlet hose respectively for introducing the ultrasound transmission medium into the ultrasound transmission space and for discharging the ultrasound transmission medium from the ultrasound transmission space, and wherein the sealing member comprises through holes into which the inlet hose and the outlet hose are respectively inserted.

6. The ultrasound apparatus of claim 5, wherein the sealing member further comprises a through hole through which an electrical cable for applying an electric power to the piezoelectric element passes.

7. The ultrasound apparatus of claim 1, wherein an indication or a structure for determining an insertion position of the sealing cover is provided to at least one of the housing and the supporting rod.

8. The ultrasound apparatus of claim 1, wherein a protrusion is provided to one of the sealing cover and the supporting rod and an indentation into which the protrusion can be inserted is provided another one of the sealing cover and the supporting rod, in order to determine an insertion position of the sealing cover.

9. The ultrasound apparatus of claim 1, wherein at least one of a mark indicating an insertion depth into the body cavity and a mark indicating an irradiation direction of an ultrasound is indicated on the sealing cover.

10. The ultrasound apparatus of claim 1, wherein the sealing cover is provided with an ultrasound generation position mark which indicates a position of the piezoelectric element in a state in which the sealing cover is coupled to the ultrasound probe.

11. The ultrasound apparatus of claim 1, wherein a mark which indicates an irradiation direction of an ultrasound is provided to the handpiece.

12. The ultrasound apparatus of claim 1, wherein the sealing cover is made of a flexible film.

13. The ultrasound apparatus of claim 1, wherein the ultrasound transmission medium is liquid, and further comprising an inlet hose and an outlet hose respectively for introducing the ultrasound transmission medium into the ultrasound transmission space and for discharging the ultrasound transmission medium from the ultrasound transmission space.

14. The ultrasound apparatus of claim 1, wherein an entrance portion of the sealing cover has a widened shape.

15. The ultrasound apparatus of claim 1, wherein the piezoelectric element has a curvature about a direction perpendicular to a longitudinal direction of the supporting rod.

16. The ultrasound apparatus of claim 15, further comprising a rear cover interposed between the piezoelectric element and the sheath-shaped cover member, wherein the rear cover has a depression formed therein having a curvature corresponding to the curvature of the piezoelectric element.

* * * * *